US006968872B2

(12) United States Patent
Sakakura et al.

(10) Patent No.: US 6,968,872 B2
(45) Date of Patent: Nov. 29, 2005

(54) PROCESS FOR RECOVERING LIQUID CHEMICAL PRODUCTS IN CHEMICAL PRODUCTION FACILITY

(75) Inventors: Yasuyuki Sakakura, Minato-ku (JP); Shuhei Yada, Yokkaichi (JP); Yasushi Ogawa, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/037,451

(22) Filed: Jan. 19, 2005

(65) Prior Publication Data
US 2005/0167362 A1    Aug. 4, 2005

Related U.S. Application Data

(63) Continuation of application No. PCT/JP04/14153, filed on Sep. 28, 2004.

(30) Foreign Application Priority Data
Oct. 7, 2003    (JP)    .............................. 2003-348024

(51) Int. Cl.[7] .............................................. B65B 1/04

(52) U.S. Cl. ..................... 141/311 A; 141/86; 220/571; 137/312

(58) Field of Search .................. 141/311 A, 86–88, 141/98; 220/571; 137/312–314; 4/321, 431

(56) References Cited

U.S. PATENT DOCUMENTS

| 304,116 | A | * | 8/1884 | Menne ........................ 222/108 |
| 3,628,698 | A | * | 12/1971 | Allen et al. ................. 222/168 |
| 4,120,312 | A | * | 10/1978 | Michael .................... 137/236.1 |
| 4,660,585 | A | * | 4/1987 | Schoenhard ............... 134/96.1 |

FOREIGN PATENT DOCUMENTS

JP    2003-146936    5/2003

* cited by examiner

*Primary Examiner*—Steven O. Douglas
(74) *Attorney, Agent, or Firm*—Nixon & Vanderhye PLC.

(57) ABSTRACT

The present invention provides a process for recovering liquid chemical products, in which the residual liquid chemical products remaining in respective handling devices in a chemical production facility can be efficiently and safely recovered therefrom without leakage thereof out of the system.

In the process for recovering liquid chemical products in a chemical production facility according to the present invention, the chemical products are withdrawn from the handling devices through bottom discharge pipes (14), (15), (16) and (17) thereof, directly collected by the gravity thereof into a common inclined collection pipe (13) located at a position lower than the bottom discharge pipes and connected to the bottom discharge pipes, and then delivered by the gravity thereof through the inclined collection pipe (13) to a recovery tank (1) located at a position lower than the inclined collection pipe and connected to a lower end of the inclined collection pipe.

7 Claims, 1 Drawing Sheet

PROCESS FOR RECOVERING LIQUID CHEMICAL PRODUCTS IN CHEMICAL PRODUCTION FACILITY

This application is a continuation of international application PCT/JP2004/14153 filed Sep. 28, 2004 which claims benefit of Japanese Application No. 2003-384024 filed Oct. 7, 2003, the entire content of which is hereby incorporated by reference.

TECHNICAL FIELD

The present invention relates to a process for recovering liquid chemical products in a chemical production facility, and more particularly, to a process for efficiently and safely recovering residual chemical products from respective handling devices in a chemical production facility for dealing with liquid chemical products such as acrolein and acrylic acid at a preparatory stage before operation of the facility as well as during or after the operation thereof.

BACKGROUND ARTS

Chemical production facilities for dealing with liquid chemical products such as acrylic acid, include various handling devices such as reactors, distillation columns, storage tanks and other equipments fitted thereto such as pumps (refer to Japanese Patent Application Laid-open (KOKAI) No. 2003-146936). In the chemical production facilities, the liquid chemical products have been sampled from the respective handling devices during operation thereof, and subjected to inspection and analysis to check results of reaction in the operating reactors as well as qualities of distillates and bottom liquids obtained from the distillation columns. Also, in the case where the chemical production facilities are stopped for inspection and repair thereof, the chemical products are discharged from the respective devices into containers, etc., by means of a pump. In particular, if (meth)acrolein, (meth)acrylic acid, (meth) acrylic acid esters, etc., remain even in a very small amount in the handling devices or conduits, these substances tends to be polymerized and form solids therein, resulting in clogging of the devices or conduits. Therefore, these substances must be surely removed from the handling devices or conduits after stopping the operation of the facilities.

DISCLOSURE OF THE INVENTION

Problem to be Solved by the Invention

Meanwhile, in the chemical production facilities, the liquid chemical products are individually withdrawn from the respective handling devices into containers, etc. For this reason, in some operating procedures, there is caused such a risk that the chemical products are exposed to atmospheric air, resulting in environmental pollution due to scattering of vapor thereof as well as contamination of working environment due to scattering of the toxic or malodor substances. In addition, in the case where the chemical products have a flashing point lower than a liquid temperature within the respective handling devices, there is also caused such a risk that a detonating gas is formed upon discharging the liquid chemical products therefrom into containers, etc.

The present invention has been made in view of the above conventional problems. An object of the present invention is to provide a process for recovering liquid chemical products as residues remaining in respective handling devices of a chemical production facility which is capable of efficiently and safely recovering the liquid chemical products without leakage thereof out of the system.

Means for Solving the Problem

In the present invention, upon recovering liquid chemical products from respective handling devices in a chemical production facility, in order to prevent contamination of ambient environment and working environment, the liquid chemical products are discharged from the handling devices through respective bottom discharge pipes and directly collected by the gravity thereof into a common inclined collection pipe, and then delivered by the gravity thereof through the inclined collection pipe toward a recovery tank located at a lowermost position of the chemical production facility.

That is, according to the aspect of the present invention, there is provided a process for recovering liquid chemical products in a chemical production facility including a plurality of handling devices therefor, in which the residual chemical products are recovered from the respective handling devices, comprising:

withdrawing the chemical products from the respective handling devices through bottom discharge pipes thereof;

collecting the thus withdrawn chemical products into a common inclined collection pipe located at a position lower than the bottom discharge pipes and connected to the bottom discharge pipes; and delivering the chemical products through the inclined collection pipe to a recovery tank located at a position lower than the inclined collection pipe and connected to a lower end of the inclined collection pipe.

Effect of the Invention

According to the present invention, upon recovering chemical products remaining as residues in respective handling devices in a chemical production facility for dealing with liquid chemical products, a common inclined collection pipe is provided so that the chemical products are directly collected by the gravity thereof into the inclined collection pipe from the respective handling devices and then recovered therethrough into a recovery tank. Therefore, it is possible to efficiently and safely recover the liquid chemical products without leakage thereof out of the system and occurrence of malodor.

EXPLANATION OF REFERENCE NUMERALS

Figure 1:
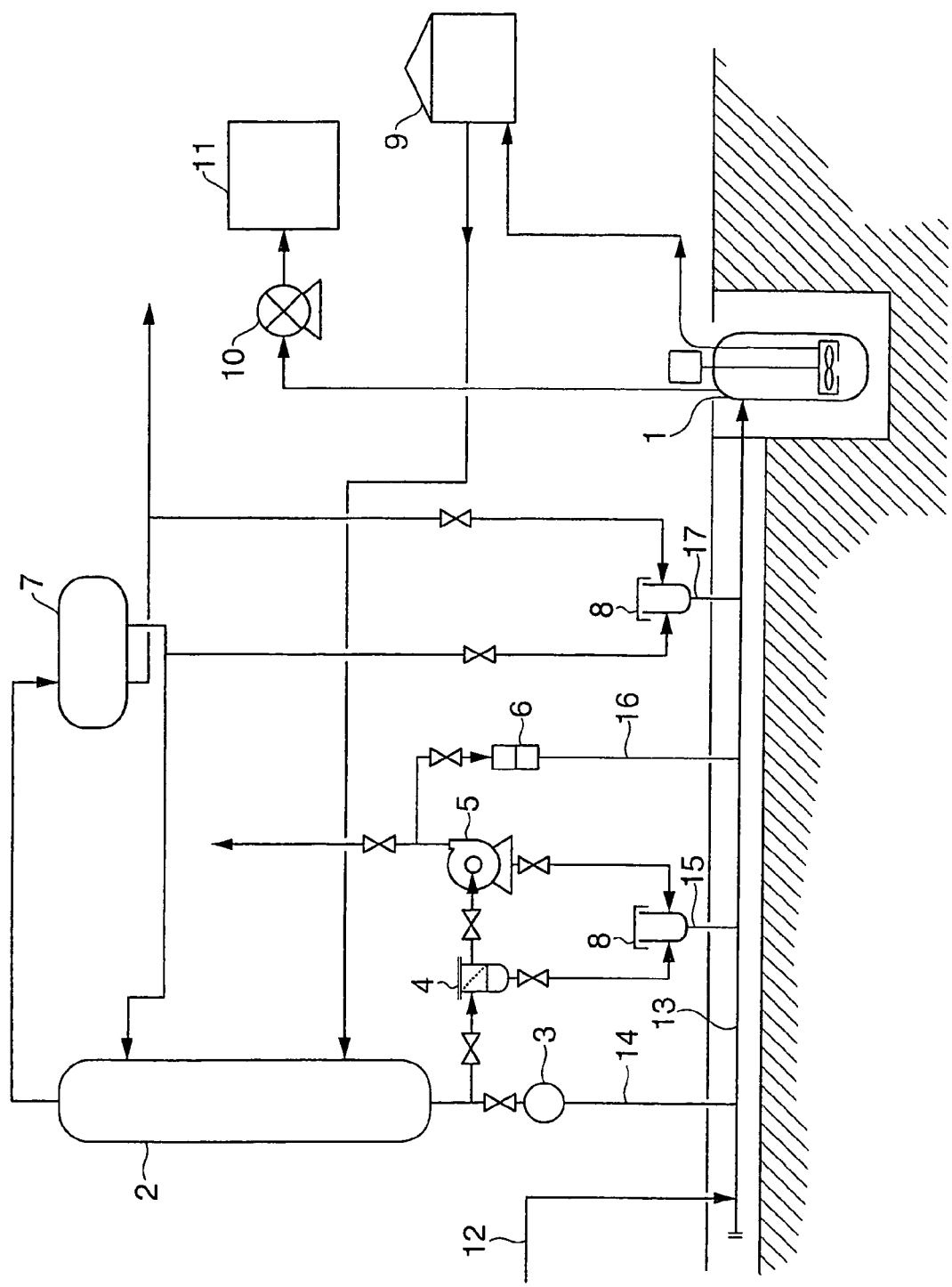
FIG. 1 is a flow diagram showing a chemical production facility suitably used in a process for recovering liquid chemical products according to the present invention.

1: Recovery tank; 10: Blower; 11: Waste (gas) treatment device; 12: Feed line for incombustible gas; 13: Inclined collection pipe; 14: Bottom discharge pipe; 15: Bottom discharge pipe; 16: Bottom discharge pipe; 17: Bottom discharge pipe; 2: Distillation column; 3: Sight glass; 4: Strainer; 5: Pump; 6: Sampling box; 7: Storage tank; 8: Drain pot; 9: Tank

PREFERRED EMBODIMENT FOR CARRYING OUT THE INVENTION

The preferred embodiments of the present invention will be explained below by referring to the accompanying drawing. FIG. 1 is a flow diagram showing a chemical production facility suitably used in the process for recovering liquid chemical products according to the present invention. In the following descriptions, the process for recovering liquid chemical products in a chemical production facility is referred to merely as a "recovery process".

The recovery process of the present invention is such a process wherein in a chemical production facility including a plurality of handling devices for dealing with liquid chemical products, the residual chemical products are efficiently and safely recovered from the respective handling devices. In the present invention, examples of the liquid chemical products may include liquid organic chemical products exhibiting a vapor pressure at ordinary temperature (25° C.), in particular, such organic chemical products exhibiting a vapor pressure of 0.01 to 50 kPa at the ordinary temperature. In addition, examples of the chemical products suitably handled by the process of the present invention may include combustible liquid organic chemical products, more specifically, toxic substances such as acrolein as well as combustible substances having a strong odor and a low threshold concentration as to odor such as (meth)acrylic acid and (meth)acrylic acid esters. In the present invention, examples of the handling devices may include devices or equipments capable of performing various treatments such as reactors, distillation columns, absorption columns, stripping columns, rectifying columns, separators, extraction columns, adsorption columns, collection columns and storage tanks.

The recovery process of the present invention can be applied, for example, to the chemical production facility as shown in FIG. 1. The chemical production facility illustrated in FIG. 1 is a facility for production of acrylic acid, in which an aqueous acrylic acid solution obtained by oxidation reaction of propylene or propane is purified, and includes various handling devices mainly constituted by a distillation column (2) for distilling the aqueous acrylic acid solution, a pump (5) for withdrawing a bottom liquid from the distillation column, a strainer (4) for separating polymers of acrylic acid (solids) produced in the distillation column (2), a storage tank (7) for storing distillates obtained from the distillation column (2), etc.

More specifically, the distillation column (2) may be an azeotropic separation column for distilling the aqueous acrylic acid solution with an azeotropic solvent such as toluene, methyl isobutyl ketone and acetic acid esters which is provided at a bottom thereof with a discharge pipe connected to the strainer (4) and the pump (5) for withdrawing a bottom liquid therefrom. The bottom liquid withdrawn through the discharge pipe is delivered to a facility for the subsequent step (not shown) by means of the pump (5). The storage tank (7) may be a tank for storing the distillates obtained from the distillation column (2). The distillates stored in the storage tank may be fed as reflux or effluent to the distillation column (2) or the other facilities.

The distillation column (2) is further provided at the bottom thereof with a drain nozzle for withdrawing distillation residues therefrom, which is connected at a tip end thereof to a bottom discharge pipe (14) through a sight glass (3). The strainer (4) is provided for separating solids which tend to be produced upon heating the easy-polymerizable substances such as (meth) acrylic acid and (meth)acrylic acid esters in the distillation column (2). The strainer (4) may be, for example, of a bucket type, in particular, preferably such a type having a large-volume wire-netting portion. The strainer (4) and the pump (5) are respectively connected at the bottom thereof with drainpipes for discharging residues therefrom. These drainpipes are connected with a drain pot (8) that is provided inside thereof with a perforated plate for separating solids from the residues. The drain pot (8) may be such a device for observing and ascertaining the condition of waste water discharged therethrough by opening a lid thereof. The drain pot (8) is provided at a bottom thereof with a bottom discharge pipe (15) for discharging the residues from the drain pot.

Also, the pump (5) is connected at an outlet side thereof to a sampling box (6) through a branched pipe for sampling a part of the bottom liquid fed from the distillation column (2). Thus, the liquid chemical products are sampled during the operation of the facility into the sampling box (6) to inspect and analyze a quality thereof as well as a concentration of impurities therein, so that it becomes possible to ascertain whether or not the distillation column (2) is suitably operated. Upon sampling, the sampling box (6) is opened at its door to receive a container therein, and then a sample is extracted into the container through a sampling nozzle by actuating a valve located on an upstream side thereof. The sampling box (6) is provided at a bottom thereof with a bottom discharge pipe (16) for discharging residues remaining in the branched pipe connected to the outlet side of the pump (5) and the sampling box.

The storage tank (7) for storing the distillates is fitted at a bottom thereof with a drainpipe for discharging the residual distillates. The drainpipe is connected to a drain pot (8) for ascertaining discharge of the liquid. The drain pot (8) is provided at a bottom thereof with a bottom discharge pipe (17) for discharging residues from the drain pot. In addition, the drainpipe of the storage tank (7) may also be provided with a sight glass as mentioned above.

Meanwhile, if any chemical products such as (meth) acrolein, (meth)acrylic acid and (meth)acrylic acid esters remain in the handling devices or conduits, these substances tend to be polymerized to form solids therein, resulting in clogging of the handling devices or conduits. Therefore, after stopping the operation of the facility, the residual chemical products must be surely removed from the respective handling devices or conduits. Also, upon inspection or repair of the handling devices, the above chemical products must be surely removed therefrom.

For these reasons, in the above chemical production facility, in order to efficiently and safely recover the chemical products, the bottom discharge pipes (14), (15), (16) and (17) of the respective handling devices are connected to a common inclined collection pipe (13) which is installed at a position lower than the bottom discharge pipes, and serves for collecting the chemical products discharged and delivering the same therethrough. Further, at a position still lower than the inclined collection pipe (13), there is installed a recovery tank (1) connected to a lower end of the inclined collection pipe for recovering the chemical products delivered through the inclined collection pipe together. In the chemical production facility as shown in FIG. 1, from the standpoints of ensuring safety and preventing environmental pollution, the withdrawal of the chemical products to the inclined collection pipe (13) from the bottom discharge pipes (14), (15), (16) and (17) as well as the delivery of the chemical products to the recovery tank (1) through the inclined collection pipe (13) may be conducted in a closed system.

The flashing point of acrolein is −18° C., the flashing point of methyl acrylate is −2.8° C., the flashing point of ethyl acrylate is 15,5° C. and the flashing point of methyl methacrylate is 10° C. (Meth)acrylic acid itself has a flashing point of not lower than 50° C. However, since (meth) acrylic acid is produced using a solvent having a low flashing point such as toluene, methyl isobutyl ketone, acetic acid esters or the like during the production process, the resultant reaction mixture exhibits a flashing point lower than that of (meth)acrylic acid solely. For example, among the above solvents, toluene has a flashing point of 5° C. In addition, (meth)acrolein and (meth)acrylic acid esters have a very strong odor, and the odor is sensed even at a very low concentration thereof. The threshold concentrations of these substances as to sensible odor are, for example, 0.07 ppm for acrolein, 0.4 ppb for methyl acrylate, 0.21 ppm for methyl methacrylate, and 0.016 ppm for butyl methacrylate.

Therefore, in order to ensure safety and prevent environmental pollution, it is important to directly connect the inclined collection pipe (13) to the bottom discharge pipes (14), (15), (16) and (17). The inclined collection pipe (13) is installed in a trench (groove) formed on the ground, and inclined toward the recovery tank (1) with a descending slope of about $1/100$ to $3/100$ to deliver the chemical products by the gravity therethrough. As mentioned above, since the inclined collection pipe (13) is located at a position lower than the bottom discharge pipes (14), (15), (16) and (17), the liquid chemical products can be collected by the gravity thereof from the respective handling devices into the inclined collection pipe.

Also, in order to prevent the chemical products from being polymerized or fired in the inclined collection pipe (13) and the recovery tank (1), the inclined collection pipe (13) is constructed such that an incombustible gas can be fed thereinto through an incombustible gas feed line (12). As the incombustible gas, there may be used inert gases such as nitrogen gas or oxygen-containing inert gases containing oxygen at a concentration of not more than 10% by volume. For example, in the facilities for production of acrylic acid, a mixed gas composed of air and nitrogen whose oxygen concentration is controlled to 10% by volume may be fed to the inclined collection pipe (13). Meanwhile, a plurality of the inclined collection pipes (13) may be installed so as to cover a whole portion of the chemical production facility.

It is required that the recovery tank (1) is installed at a position still lower than the inclined collection pipe (13). More specifically, the recovery tank (1) is located below the ground level, for example, within a pit formed under the ground. As the recovery tank (1), there may be usually used a vertical-type storage tank as shown in FIG. 1. Further, there may also be used a horizontal-type storage tank or a pit-type storage tank made of concrete, etc., which is directly constructed under the ground. Meanwhile, a plurality of the recover tanks (1) may be installed depending upon conditions of arrangement of the handling devices or installation sites thereof.

The recovery tank (1) is provided with a liquid discharging means for discharging the liquid chemical products as recovered to a regeneration step or a waste (gas) treatment device and a gas discharging means for discharging gases generated from the recover tank to an effective ingredient recovery step or the waste (gas) treatment device. In the chemical production facility as shown in FIG. 1, from the standpoints of ensuring safety and preventing environmental pollution, the discharge of the chemical products and gases from the recovery tank (1) may be conducted in a closed system.

The above liquid discharging means may be usually constituted by a pump inserted into the recovery tank (1). As the pump, there may be used not only a submerged type pump as illustrated in FIG. 1, but also an ordinary centrifugal pump. The pump may be operated on or off in response to signals generated from a level gauge such that the chemical products are fed to a tank (9) when the liquid level in the recovery tank (1) is raised to a predetermined height. In the above chemical production facility, the chemical products recovered in the recovery tank (1) are temporarily collected in the tank (9) by means of the pump, and then fed again to the regeneration step, i.e., the distillation column (2) in the case of the facility as shown in FIG. 1, to separate and recover effective ingredients therefrom, or fed to the purification device (not shown) for disposal treatment thereof. Meanwhile, as the liquid discharging means, a pressure feeding means using pressurized nitrogen or air may be used instead of the pump.

The above gas discharging means may be constituted by a gas discharge conduit extending from an upper portion (gas-phase portion) of the recovery tank (1) toward a waste (gas) treatment device (11) and a blower (10) fitted to the gas discharge conduit. When an inside pressure of the recovery tank (1) exceeds an ordinary pressure, gases in the recovery tank tend to be leaked therefrom. For this reason, the inside of the recovery tank (1) may be sucked or evacuated by the blower (10) to control the inside pressure of the recovery tank to usually not more than ordinary pressure, preferably not more than −10 kPa. In order to maintain a constant inside pressure of the recovery tank (1), the amount of gases discharged therefrom is preferably controlled by detecting the inside pressure of the recovery tank at real time. From the viewpoint of simplicity, there may be used a method of fitting a restricted orifice, etc., to the above gas discharge conduit to establish a flow resistance therein, or a method of sucking or evacuating the gases when the pressure becomes a predetermined value. In the above chemical production facility, the gases discharged from the recovery tank (1) is fed to the waste (gas) treatment device (11) where the gases are converted into harmless ones, and then discharged to atmosphere.

Alternatively, in the above chemical production facility, the gases discharged from the recovery tank (1) may be fed back to the effective ingredient recovery step (not shown) provided on the production facility side to recover effective ingredients therefrom. For example, in the facilities for production of (meth)acrolein or (meth)acrylic acid, an absorption column capable of absorbing (meth)acrolein or (meth)acrylic acid with water from oxidation reaction gases may be provided, and the gases discharged from the recovery tank may be flowed back to the absorption column to recover effective ingredients therefrom. Meanwhile, in the above chemical production facility, by providing the gas discharging means in the recovery tank (1), it becomes possible to suck or absorb gases partially vaporized in the sampling box (6), etc., during the sampling, into the recovery tank (1) through the inclined collection pipe (13), thereby preventing contamination of ambient environment.

As described above, the recovery process of the present invention which can be carried out in the chemical production facility as illustrated in FIG. 1, is such a process for recovering chemical products in which the chemical products are withdrawn through the bottom discharge pipes (14), (15), (16) and (17) of the respective handling devices, collected into the common inclined collection pipe (13) which is located at a position lower than the bottom discharge pipes and connected to the bottom discharge pipes, and delivered through the inclined collection pipe (13) to the recovery tank (1) which is located at a position lower than the inclined collection pipe (13) and connected to a lower end of the inclined collection pipe. In such a process, the chemical products are directly collected by the gravity thereof through the bottom discharge pipes (14), (15), (16) and (17) of the respective handling devices into the inclined collection pipe (13), and delivered by the gravity thereof through the inclined collection pipe (13) to the recovery tank (1) located at the lowermost position in the chemical production facility. Therefore, according to the recovery process of the present invention, the chemical products remaining as residues in the respective handling devices can be efficiently and safely recovered without leakage thereof out of the system and occurrence of malodor.

Further, according to the recovery process of the present invention, when the chemical products are delivered through the inclined collection pipe (13) to the recovery tank (1), an incombustible gas is fed through the inclined collection pipe (13). As a result, it is possible to effectively prevent polymerization of the chemical products or formation of a detonating gas in the inclined collection pipe (13) and the recovery tank (1). In addition, in the recovery process, after delivering the chemical products to the recovery tank (1), the chemical products are discharged from the recovery tank (1) to the regeneration step or the waste (gas) treatment device by the liquid discharging means, and the gases generated therein are discharged from the recovery tank (1) to the effective ingredient recovery step or the waste (gas) treatment device (11) by the gas discharging means. With this arrangement, even such chemical products having a low flashing point can be treated safely, and ambient environment can be prevented from being contaminated. As described above, the recovery process of the present invention can be suitably applied to facilities for production of (meth)acrolein, (meth)acrylic acid or (meth)acrylic acid esters, which tend to be readily polymerized and have a low flashing point.

What is claimed is:

1. A process for recovering liquid chemical products in a chemical production facility including a plurality of handling devices therefor, in which the residual chemical products are recovered from the respective handling devices, comprising:

withdrawing the chemical products from the respective handling devices through bottom discharge pipes thereof;

collecting the thus withdrawn chemical products into a common inclined collection pipe located at a position lower than the bottom discharge pipes and connected to the bottom discharge pipes; and delivering the chemical products through the inclined collection pipe to a recovery tank located at a position lower than the inclined collection pipe and connected to a lower end of the inclined collection pipe.

2. A process according to claim 1, wherein the recovery tank is located at a position below ground level.

3. A process according to claim 1, wherein an incombustible gas is fed to the inclined collection pipe upon delivering the chemical products to the recovery tank through the inclined collection pipe.

4. A process according to claim 1, wherein the withdrawal of the chemical products through the bottom discharge pipes and the delivery of the chemical products to the recovery tank are conducted in a closed system.

5. A process according to claim 1, wherein after delivering the chemical products to the recovery tank, the chemical products are discharged from the recovery tank to a regeneration step or a waste treatment device by a liquid discharging means, and gases generated in the recovery tank are discharged therefrom to an effective ingredient recovery step or the waste treatment device by a gas discharging means.

6. A process according to claim 5, wherein the discharge of the chemical products and the gases from the recovery tank is conducted in a closed system.

7. A process according to claim 1, wherein the chemical products are (meth)acrolein, (meth)acryiic acid or (meth)acrylic acid esters.

* * * * *